(12) United States Patent
Godsmark et al.

(10) Patent No.: US 8,742,192 B2
(45) Date of Patent: Jun. 3, 2014

(54) OLIGOMERISATION OF OLEFINS WITH ZEOLITE CATALYST

(75) Inventors: John S. Godsmark, Grez Doiceau (BE); Raphael F. Caers, Edegem (BE); Jihad M. Dakka, Whitehouse Station, NJ (US); Hans K. T. Goris, Laakdal (BE); Marc P. H. Puttemans, Schepdaal (BE); Stephen H. Brown, Bernardsville, NJ (US); Georges M. K. Mathys, Bierbeek (BE); Paul Hamilton, Brussels (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 1497 days.

(21) Appl. No.: 11/914,656

(22) PCT Filed: Jun. 16, 2006

(86) PCT No.: PCT/EP2006/005851
§ 371 (c)(1),
(2), (4) Date: Apr. 15, 2008

(87) PCT Pub. No.: WO2007/006398
PCT Pub. Date: Jan. 18, 2007

(65) Prior Publication Data
US 2012/0116141 A1 May 10, 2012

(30) Foreign Application Priority Data
Jun. 17, 2005 (GB) .................................. 0512377.3

(51) Int. Cl.
*C07C 2/12* (2006.01)

(52) U.S. Cl.
USPC ........... 585/533; 585/520; 585/530; 585/532; 422/198; 422/202

(58) Field of Classification Search
USPC .......... 585/502, 520, 530, 532, 533; 422/198, 422/202
See application file for complete search history.

(56) References Cited

U.S. PATENT DOCUMENTS 2,850,360 A 5/1956 Bottenberg
3,510,539 A 5/1970 Fernald et al.
(Continued)

FOREIGN PATENT DOCUMENTS

EP 0 716 887 6/1996
EP 0746538 12/1996
(Continued)

OTHER PUBLICATIONS

Edgar, et al., "Process Control" in Perry's Chemical Engineer's Handbook, 7th ed., McGraw-Hill, 1997, available on-line at www.knovel.com.*

(Continued)

*Primary Examiner* — In Suk Bullock
*Assistant Examiner* — Bradley Etherton
(74) *Attorney, Agent, or Firm* — Andrew B. Griffis; Leandro Arechederra

(57) ABSTRACT

The conversion and run length for oligomerization of olefins over a molecular sieve catalyst in a tubular reactor is improved by controlling the peak temperature to not exceed 50 degrees C. above the temperature of the temperature control fluid exiting the shell side outlet of the reactor. A tubular reactor containing molecular sieve catalyst is provided with a multipoint thermocouple in at least one tube, and optionally with a bottom design adapted for fast unloading of the molecular sieve catalyst from the tubular reactor.

17 Claims, 5 Drawing Sheets

(56) References Cited

U.S. PATENT DOCUMENTS

Figure 1:
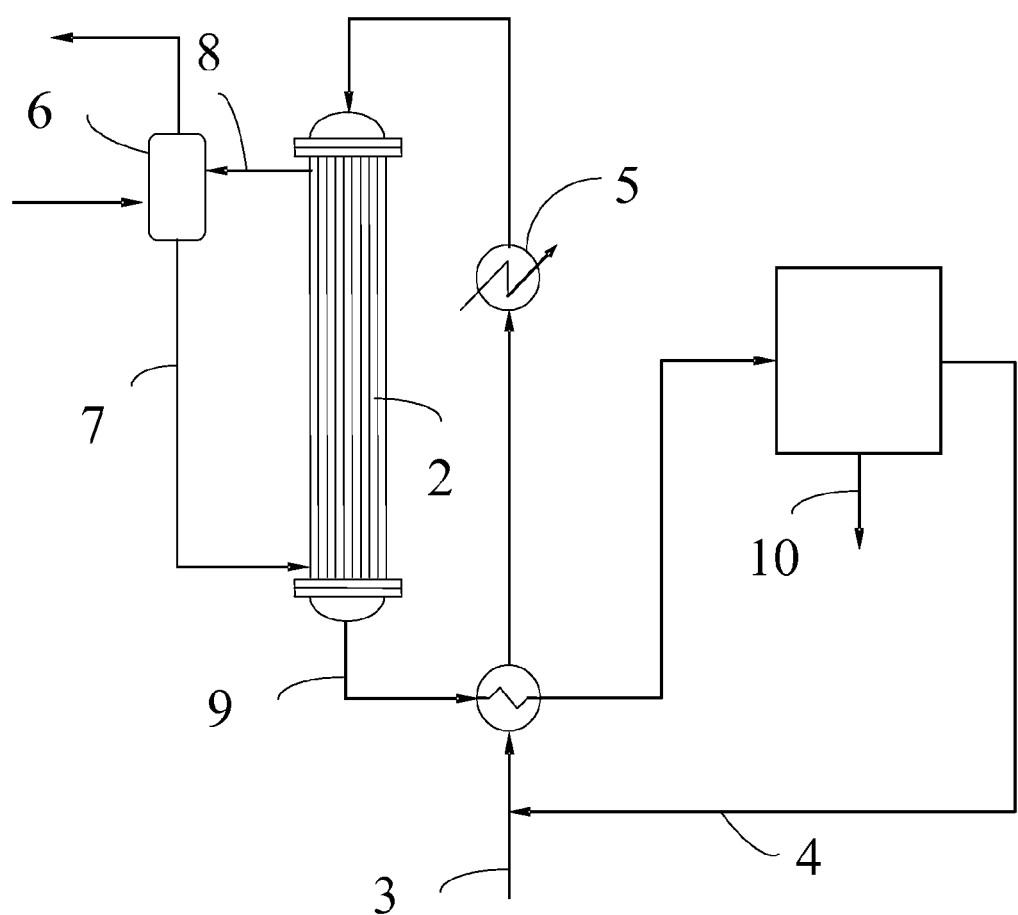

| | | | |
|---|---|---|---|
| 4,308,414 A * | 12/1981 | Madgavkar et al. | 585/525 |
| 4,440,509 A * | 4/1984 | Agarwal | 374/166 |
| 4,456,781 A * | 6/1984 | Marsh et al. | 585/533 |
| 4,544,788 A * | 10/1985 | Daviduk et al. | 585/501 |
| 4,560,536 A * | 12/1985 | Tabak | 422/116 |
| 4,709,111 A * | 11/1987 | Ward | 585/503 |
| 5,672,800 A * | 9/1997 | Mathys et al. | 585/520 |
| 5,990,367 A | 11/1999 | Stine et al. | |
| 6,072,093 A | 6/2000 | O'Neill et al. | |
| 6,080,903 A | 6/2000 | Stine et al. | |
| 6,550,963 B2 * | 4/2003 | Daily et al. | 374/179 |
| 6,884,914 B2 | 4/2005 | Mathys et al. | |
| 2003/0129123 A1 | 7/2003 | Ramani et al. | |
| 2006/0270882 A1 | 11/2006 | Brown et al. | |

FOREIGN PATENT DOCUMENTS

| | | |
|---|---|---|
| EP | 0 808 298 | 11/1997 |
| EP | 0 989 106 | 3/2000 |
| WO | 96/15983 | 5/1996 |
| WO | WO03/082780 | 10/2003 |
| WO | WO/2005/058782 | 6/2005 |
| WO | WO2005/058787 | 6/2005 |
| WO | WO2005/118512 | 12/2005 |
| WO | WO2005/118513 | 12/2005 |

OTHER PUBLICATIONS

Chitnis et al., "ExxonMobil Olefins to Gasoline: EMOGAS Technology for Catpoly Units," Proceedings of the National Petrochemical and Refiners Association, Mar. 13-15, 2005, Hilton Hotel, San Francisco, California, USA.

* cited by examiner

OLIGOMERISATION OF OLEFINS WITH ZEOLITE CATALYST

CROSS REFERENCE TO RELATED PATENT APPLICATIONS

This application is a national stage filing of International Patent Cooperation Treaty Application No. PCT/EP2006/005851 filed Jun. 16, 2006, which claims priority from Great Britain Application 0512377.3 filed Jun. 17, 2005, the disclosure of which is fully incorporated herein by reference.

FIELD OF THE INVENTION

The present invention relates to improvements in or relating to the oligomerisation of olefins and in particular to the oligomerisation of olefins performed in a tubular reactor and over a zeolite catalyst.

BACKGROUND OF THE INVENTION

The condensation reaction of an olefin or a mixture of olefins over an acid catalyst to form higher molecular weight products is a widely used commercial process. This type of condensation reaction is referred to herein as an oligomerisation reaction, and the products are low molecular weight oligomers which are formed by the condensation of up to 12, typically 2, 3 or 4, but up to 5, 6, 7, or even 8 olefin molecules with each other. As used herein, the term 'oligomerisation' is used to refer to a process for the formation of oligomers and/or polymers. Low molecular weight olefins (such as propene, 2-methylpropene, 1-butene and 2-butenes, pentenes and hexenes) can be converted by oligomerisation over a zeolite catalyst, to a product which is comprised of oligomers and which is of value as a high-octane gasoline blending stock and as a starting material for the production of chemical intermediates and end-products. Such chemical intermediates and end-products include alcohols, acids, detergents and esters such as plasticiser esters and synthetic lubricants. Industrial oligomerisation reactions are generally performed in a plurality of tubular or chamber reactors. Sulphated zirconia, liquid phosphoric acid and sulphuric acid are also known catalysts for oligomerisation.

Industrial hydrocarbon conversion processes employing zeolite catalysts typically run for several weeks before a catalyst change is required or a decommissioning of the reactor is needed. In industrial processes the feeds for the reactions are generally obtained from refining activities such as a stream derived from catalytic or steam cracking, which may have been subjected to fractionation. The nature of such refining activities is such that there will be variations in the composition of the feed. In addition it may be desired to change the nature of the feed during a reactor run. The catalyst activity and the reaction conditions vary according to the composition of the feed. Furthermore, the reactions are exothermic and the size of the exotherm also depends upon the nature and amount of olefin present in the feed. Isobutylene and propylene are particularly reactive generating a large amount of heat per unit of mass reacting.

The present invention is concerned with such processes that employ a zeolite oligomerisation catalyst in a tubular reactor and is particularly concerned with the provision of reaction conditions which enhance the conversion of the reaction.

Our copending applications PCT/EP/2005/005784, published as WO2005/118513, and PCT/EP/2005/005785, published as WO2005/118512, are also concerned with oligomerisation of feeds containing higher olefin content and they employ particular catalyst systems to achieve this end.

Tubular oligomerisation reactors employing zeolite catalysts typically comprise one or more bundles of tubes also termed "reactor tubes", mounted, preferably vertically, within a shell. The tubes are packed with the zeolite catalyst typically in the form of pellets and the olefin reactant is passed through the tubes in which it is oligomerised, typically from top to bottom. The length of the tube in industrial practice, is generally from 2 to 15 meters. The diameter of the tube, the thickness of the walls of the tubes and the materials from which the tubes are made are important since oligomerisation reactions are exothermic and it is important to dissipate the heat generated by the oligomerisation reaction. Accordingly relatively small diameter tubes, such as those having an internal diameter from 25 to 75 mm, are preferred, more preferably 35 to 50 mm diameter tubes. The reactor tubes are preferably of high strength material and are thin walled and of a material with a high thermal conductivity. The high strength is required to withstand the high pressures that are generally used in the oligomerisation of olefins in a tubular reactor employing a zeolite catalyst. Duplex stainless steel is a preferred material for manufacture of the tubes.

Any convenient number of tubes may be employed in a reactor shell. Typically, operators use from 10 to 500 tubes per shell, preferably arranged in parallel. Preferred reactors contain about 77 tubes or 180 tubes per shell, although any number may be employed to suit the needs of the operator, e.g. 360 or 420. The tubes are preferably mounted within the shell and a temperature control fluid is provided around the outside of the tubes but within the shell to dissipate heat generated by the exothermic reaction that, in use, takes place within the reactor tubes. One reactor may comprise multiple bundles of tubes, for example up to 7 or 8, or even 9 bundles, and preferably, in use, the temperature of the fluid within the tubes in all the bundles in the same reactor is controlled by means of the same temperature control fluid system.

Reference in this specification to removal of heat from the (reactor) tubes or temperature control of the (reactor) tubes is, in context, intended to mean removal of heat from the materials contained within the tubes where reaction takes place (generally comprising, in use, unreacted feed, reaction products and catalyst) and control of the temperature of those materials contained within the tubes. It will be appreciated that the heat generation on the catalyst and heat removal from the tube wall may cause a radial temperature gradient through the cross-section of the tube, such that the centre of the tube may become significantly hotter than the wall of the tube. One convenient way to remove the heat from the tubes and carry out the temperature control is to generate steam within the reactor on the shell side around the exterior of the tubes. This provides a good heat transfer coefficient on the shell side. If the present invention is performed in a chemical plant or a refinery, the steam generated by the oligomerisation process may be readily integrated into the steam system typically present at such sites. The reaction heat from oligomerisation may then be put to use in another part of the oligomerisation process, or with another process in the plant or the refinery, where heat input is required.

On an industrial scale it is desirable that these tubular reactors can run continuously for as long as possible and that the conversion and selectivity of the reaction is maintained over such extended production runs.

U.S. Pat. No. 6,884,914 relates to the oligomerisation of olefins and provides an olefin feed stream which can be oligomerised at high efficiency. The olefin feed stream may be obtained from oxygenates by treatment with mole sieves.

However, although refining feeds may also be used, these are preferably used in admixture with the olefin feed obtained from the oxygenates. The feed preferably contains about 55 wt % olefin and more preferably 60 wt % olefins. U.S. Pat. No. 6,884,914 discusses various different catalysts that can be employed and zeolite catalysts are preferred. The oligomerisation reaction is performed at a temperature from 170° C. to about 300° C. preferably about 170° C. to 260° C. most preferably about 180° C. to about 260° C. Operating pressure is said to be not critical although the process is carried out at about 5 MPa to 10 MPa. In the oligomerisations exemplified in U.S. Pat. No. 6,884,914, a feed containing 64 wt % butenes is oligomerised using a ZSM-22 zeolite catalyst. This reaction will be less exothermic than oligomerisation of propylene or isobutylene over a solid phosphoric acid catalyst.

U.S. Pat. No. 6,884,914 is not, however, concerned with optimising oligomerisation of olefins in a tubular reactor. Tubular reactors are the most efficient for oligomerisation reactions over zeolite catalyst because the reactions are highly exothermic and require precise temperature control.

U.S. Pat. No. 5,672,800 (WO 93/16020) is concerned with the oligomerisation of olefins employing a zeolite catalyst, particularly the zeolite ZSM-22. U.S. Pat. No. 5,672,800 indicates that conversion and catalyst life can be improved if the oligomerisation is performed in the presence of water. The compositions in the examples show a significant improvement when water is present, U.S. Pat. No. 5,672,800 is not however concerned with oligomerisation in tubular reactors and we have found that the use of the water in tubular reactors according to U.S. Pat. No. 5,672,800 can lead to undesirable corrosion of the reactors or downstream equipment, as the water may combine with olefins in the feed and via a complex reaction mechanism lead to the formation of organic acids such as acetic, propionic and/or butyric acids. The maximum conversion achieved using the techniques of U.S. Pat. No. 5,672,800 is 1240 tonnes of oligomer per tonne of catalyst and more typical conversions are considerably less.

As already indicated, the oligomerisation of olefins over zeolite catalyst is a highly exothermic reaction, particularly the oligomerisation of propylene and/or isobutylene. The high temperatures generated can lead to carbonaceous deposits on the catalyst caused by a build up of condensed, heavy hydrocarbons similar to asphalt. Such deposits are commonly termed "coke", and lead to deactivation of the zeolite catalyst. In general, the higher the concentration of olefin in the feed, the higher will be the rate of heat release from the catalysed reaction, and hence the higher the temperatures reached. Consequently there will be a higher rate of coke formation. This has placed a limit on the maximum concentration of olefin that can be tolerated in the feed.

The ExxonMobil Olefins to Gasoline (EMOGAS) process was described at the Annual Meeting of the National Petrochemical and Refiners Association, 13 to 15 Mar. 2005, at the Hilton Hotel, San Francisco, Calif., USA. The paper described olefin oligomerisation in a tubular reactor employing a zeolite catalyst and specified that the reaction temperature is controlled with water that is fed on the shell side of the reactor. It is stated that the heat released due to EMOGAS reactions in the tubes evaporates water on the shell side. The temperature profile in the tubular reactor is said to be close to isothermal and the temperature is controlled via the shell side water pressure, which controls the temperature of evaporation, and also by the reactor feed temperature. The tubular reactors are said to usually operate at a pressure between 5.5 and 7.6 MPa (800 and 1100 psi) and temperatures around 204° C. (400° F.).

The present invention is concerned with the reduction in the temperature fluctuations along the length of the reactor tube and control of the temperature along the length of the reactor tube in order to enhance the life of the catalyst and the conversion achieved. The life and conversion are assessed as the number of tons of oligomer that can be produced per ton of zeolite catalyst before the olefin conversion falls below an economically acceptable level. The invention is concerned with the conditions to be used to sustain the activity of any zeolite catalyst unlike the EMOGAS paper which specifies a particular catalyst that is more stable. The invention is also concerned to provide conditions that enable extended production runs with feeds high in olefin concentration employing conventional zeolite catalysts.

The composition of the material in the tubular reactor varies as the material flows through, usually down, the reactor tube and begins to react. The olefin will have a lower molecular weight at the beginning (inlet) of the reactor tube, where it is predominantly unreacted light olefins and it will become progressively heavier towards the tube outlet as the light olefins are oligomerised to form higher molecular weight olefins. Excessive temperatures caused by the exotherm of the reaction can coke up the catalyst, which leads to deactivation.

In the operation of a tubular reactor for oligomerisation of olefin feed, with zeolite catalyst in the tubes and a temperature control fluid on the shell side, a temperature profile will be observed over the length of a reactor tube. Conventionally, such operation is performed with the tubular reactor arranged such that the feed inlet is at the top and the reaction product outlet is at the bottom. The following description addresses such an arrangement, but it will be understood that the description applies equally to reactors not in top to bottom arrangement. Thus, the temperature profile initially increases at the inlet of the tube, when reaction heat is generated faster than it can be removed by the temperature control fluid around the tube. As the reactants convert further as they move along the tube and their concentration reduces, the reaction rate reduces and the rate of heat generation reduces. At the same time the temperature in the tube increases, and the heat removal rate increases. The temperature profile then typically goes through a maximum, and then shows a decline further along (down) the tube towards the outlet. As the reaction temperature declines along the tube, also heat removal rate reduces, and the temperature profile may then flatten out before the end of the catalyst bed in the tubes is reached.

With fresh zeolite catalyst, the temperature increase at the initial part (e.g. top) of the tube is sharp, and the temperature profile shows a sharp peak. The fresh catalyst at the initial part (top) of the tube performs most of the reaction. Coke will build up where the temperature is at its highest, which will deactivate the catalyst in that part of the tube. U.S. Pat. No. 5,672,800 seeks to overcome this problem by the addition of water to quench the activity of the catalyst. Without this quench the reaction rate will then reduce due to the catalyst deactivation, and hence the rate of heat generation will reduce, and hence the slope of the temperature increase in that part of the temperature profile declines. The catalyst further along (down) the tube will then see a higher concentration of unreacted reactants, and the reaction rate—and hence heat generation rate—will increase in that part of the tube. In this way the peak in the temperature profile known as "the peak temperature" will move along (down) the tube. In order to compensate for the reduced overall catalyst activity, heat removal is typically reduced by increasing the temperature of the temperature control fluid around the tube. The average temperature in the reactor and the temperature at the outlet of the tube or reactor will thereby be increased as the run progresses. In addition, the temperature of the feed delivered to the tube inlet may be adapted as well. Typically it may be increased to keep as much of the reaction as possible at as early (high) as possible a location in the catalyst bed inside the tube. The peak in the temperature profile therefore may not only move along (down) the tube as a production run proceeds but it may also become less sharp and less pronounced.

The rate of heat generation increases with higher reactant concentration. The peak in the temperature profile is therefore sharper and more pronounced when the olefin concentration in the feed to the reactor is higher. The rate of heat generation is also higher with more reactive reactants, typically with the lighter olefins such as propylene and butenes such as isobutylene. The peak in the temperature profile is therefore also sharper and more pronounced when a higher portion of the available butenes is isobutylene, or when a higher proportion of the olefins fed to the reactor is propylene. In case dienes or acetylenes are present, these are even more reactive and will increase the rate of heat generation, in particular in the upstream part of the zeolite catalyst bed. We have also found that cyclopentene generates the same heat of reaction as pentadiene. The total heat of the reaction also depends on the product produced. The greater the degree of oligomerisation of any particular olefin the higher the heat of reaction, because more monomer molecules will have combined to form the product.

The level of di- and polyunsaturates in the feed is typically controlled to below a maximum allowable level. Preferably, the feed composition is limited to containing no more than 100 ppm by weight of acetylene and/or no more than 500 ppm of the C3 polyunsaturates methylacetylene and propadiene or allene, and/or no more than 2500 ppm or more preferably no more than 1000 ppm of butadiene. The reason for these limitations is the high reactivity and extreme coke forming properties of the di- and poly-unsaturates. We have found that if it is necessary to use feeds containing relatively high levels of polyunsaturates, production may be sustained if the olefin concentration in the feed is reduced accordingly. This keeps the carbon deposition low which would otherwise increase due to the heat generated by the reaction of the higher amounts of polyunsaturates present.

The olefin feed to the tubular reactor is generally a mixture of a reactive olefin and an unreactive diluent, which is typically an alkane. This may have the same carbon number as the olefin. However, it is preferred to have unreactive components present that have a higher carbon number than the feed olefin because of their advantageous effect on phase behaviour in the reactor. The rate of heat generated by the oligomerisation reaction depends upon the concentration of the olefin in the feed. The higher the concentration of olefin the more reactive the feed and the greater the heat that is generated. For example in the operation of tubular reactors employing zeolite catalysts to oligomerise propylene containing feeds it has been found necessary to limit the amount of olefin in the feed. This is because, despite employing cooling systems such as the steam generation mentioned previously, it has not been possible to perform extended continuous runs with feeds containing more than 50 wt % propylene. Typically it has only been possible to employ feeds containing much less than 50 wt % propylene, some processes operating at 40 wt % propylene or less.

The feed streams containing the feed olefins such as $C_3$ and $C_4$ olefins are generally refinery steams derived from steam cracking or catalytic cracking and the composition of the stream will depend upon the raw material from which it is produced and the production technology employed. However, propylene refinery steams typically contain up to 75 or depending on severity even up to 79 wt % propylene with the balance being predominantly propane. Similarly butene refinery steams typically contain up to 70 wt % butenes with the balance being predominantly butanes. The reactivity of the olefins in oligomerisations over zeolite catalysts varies according to the nature of the olefin. However it has not been possible to successfully oligomerise $C_3$ to $C_6$ olefins over extended periods of time in tubular reactors employing a zeolite catalyst if the concentration of propylene in the feed exceeds 50 wt % and generally concentrations below 40 wt % have been employed. This has required the expensive addition of diluent to an olefin containing refinery feed. Typically the diluent may be additional amounts of the alkane found in the refinery feed and/or it maybe provided by recycle of the unreacted material derived from the tubular reactor. The need for diluent not only adds to the expense of the operation but it also reduces the volumetric yield of the reaction with associated economic debits.

There therefore remains a need to oligomerise olefin feeds containing a higher concentration of olefin using a zeolite catalyst over extended production runs in a tubular reactor without undue deactivation or premature failure of the catalyst. It will be appreciated that in large scale industrial processes such as are used for the oligomerisation of olefins, small increases in production (such as 1 to 5% increase) have highly significant benefits. In addition, the ability to increase a run length by an apparently small amount also has highly significant benefits.

Excessive peak temperature will cause coking of the catalyst which adversely impacts the conversion of the catalyst. We have now found that if the temperature and pressure within the reactor tube are controlled to within certain limits extended production runs with high conversion of olefin to oligomer may be achieved using the conventional zeolite oligomerisation catalysts with feeds containing higher levels of olefin. We have also found that if these conditions are maintained the extended runs may be achieved without the need for the presence of water. In this way the corrosion of the reactor can be reduced.

We have now developed an oligomerisation process which is capable of providing such benefits.

SUMMARY OF THE INVENTION

We have found that, regardless of what the overall, average or outlet temperatures of the reactor may be, if the peak temperature is allowed to reach too high a level, the catalyst deactivation rate becomes excessive, and the life of the catalyst bed is reduced; and that in order to obtain good catalyst life in an oligomerisation process comprising a tubular reactor containing zeolite catalyst, it is important to control the peak temperature.

The present invention therefore provides a process for oligomerising an olefin comprising contacting the olefin with a zeolite catalyst in a reactor tube of a tubular reactor having a shell that contains a temperature control fluid for removing heat of reaction from the reactor tube, in which process the olefin feed to the reactor contains at least 42 wt % of olefin, wherein operating conditions are controlled such that the reaction product mixture exiting the reactor is at a pressure of at least 55 barg and wherein the shell side temperature control fluid parameters are controlled such that the peak temperature in the reactor tube is no more than 50 degrees C. above the temperature of the temperature control fluid as said fluid exits the reactor.

In particular we prefer that the peak temperature be controlled to be no more than 40 degrees C., preferably no more than 30 degrees C., particularly preferably no more than 20 degrees C. and most preferably no more than 10 degrees C. above the temperature of the temperature control fluid as the temperature control fluid exits the reactor.

We have found that, providing those conditions are employed, feeds of single olefins and mixtures of olefins can be processed in tubular reactors employing a zeolite catalyst over extended runs, for example up to 120 days continuous operation without undesirable loss of catalytic activity. We have found that catalyst life in excess of 1200 tonnes of oligomer per tonne of catalyst may be achieved. The maximum concentration of olefin in the feed that can be processed will depend upon the nature of the olefin or mixture of olefins that are to be oligomerised. However, we have found that propylene containing feeds that contain e.g. up to 65 wt % propylene, more typically up to 60 wt % propylene, even more typically up to 55 wt %, or up to 52% or most typically up to 50 wt % propylene can be employed. Similarly we have found that butene-containing feeds that contain e.g. up to 80 wt % butene such as up to 70 wt % butene, typically up to 65 wt % butene, most typically up to 60 wt % butene can be processed. Similar amounts can be processed when mixed feeds are employed. The minimum amount of olefin in the feed, according to the invention, is preferably 42 wt %. In the case where the feed contains propylene, the more preferred minimum is 44 wt %, yet more preferably 46 wt % and most preferably 48 wt %. In the case where a butenes feed is employed, the more preferred minimum is 46 wt %, yet more preferably 50 wt %, such as at least 55 wt % and most preferably at least 60 wt %.

DETAILED DESCRIPTION OF THE INVENTION

We have found that control of the peak temperature is critical for satisfactory performance of the oligomerisation of olefins, for example $C_3$ to $C_6$ olefins, over a zeolite catalyst in a tubular reactor. The peak temperature may be measured by inserting a multipoint thermocouple in at least one of the reactor tubes. Preferably at least one centralising means, such as one or more spider-shaped inserts, may be used to keep the thermocouple substantially at the radial centre of the tube, so that it measures the highest temperature across the radial temperature profile. It is preferred that the thermocouple can detect the temperature at various locations along a significant portion of the length of the tube, preferably towards the inlet end of the tube. Desirably, temperature is measured over at least the first 50% or above, preferably at least the first 60% or 70% or possibly at least 75%, or even at least 80% or at least 85% of the length of the tube from the inlet end, and at a plurality of points. For example it is preferred to make measurements at least 5 but preferably from 10 to 20 points, such as 15 points, in a tube that is 3 to 10 meters (approx 10 to 33 feet) in length. The parameters of the temperature control fluid contained within the tubular reactor, for example the temperature and/or the flow may then be adjusted in response to the temperature measured by the thermocouples in order to maintain the peak temperature in the tube within the desired range of difference from the temperature control fluid outlet temperature. By appropriate adjustment of the parameters, this enables the process fluid temperature to be maintained at optimum conditions. When the temperature control fluid exits the reactor at about 210° C., the peak temperature is preferably maintained below 260° C., more preferably below 250° C., yet more preferably below 240° C. and most preferably below 235° C. Where the reactor consists of a number of parallel tubes, a multitude of those tubes may be provided with a multipoint thermocouple although this is not essential. When the temperature control fluid exits the reactor at about 250° C., the peak temperature is preferably maintained below 300° C., more preferably below 290° C., yet more preferably below 280° C. and most preferably below 275° C. Peak temperatures of above 325° C., preferably above 310° C., more preferably above 300° C. are less advantageous, because of cracking side reactions. So, when the temperature control fluid exits the reactor at about 300° C., the peak temperature is preferably maintained below 325° C., more preferably below 320° C., yet more preferably below 315° C. and most preferably below 310° C.

The temperature of the tubular reactors is conveniently controlled by passing a temperature control fluid around the shell side of the reactor tubes. In a preferred embodiment the tubular reactor consists of several tubes mounted vertically and in parallel and they may be mounted as a bundle or bundles of tubes. It is preferred that the olefin feed be introduced at the top of the tubes such that it passes through the tubes in a downward direction. The tubes are preferably contained within a reactor shell and the temperature control fluid preferably flows vertically upwards within the reactor shell in counter current to the direction of the flow of the olefin feed.

Alternatively arrangements may comprise co-current upflow or co-current downflow. Co-current flow of the reacting mixture and of the temperature control fluid may offer the advantage, particularly with fresh catalyst, that the temperature control fluid around the tube is colder at the end of the tube where the temperature peak occurs. This provides a better cooling at the location of the peak temperature, and improves the peak temperature control and therefore also the catalyst life.

In one embodiment of the invention the temperature control fluid may be an organic fluid such as hot oil. However, in a preferred embodiment the temperature control fluid is water, preferably maintained at pressure in the range of 5 to 85 bar gauge which results in a temperature in the range of 160 to 300° C. The temperature of the water may be controlled by varying the pressure in the stream drum that separates steam from the boiling water, provides the water for boil up on the shell side of the reactor and collects the shell side outlet stream. In this way the peak temperature wherever it may occur inside the reactor tube may be controlled to be within the desired difference from the temperature of the temperature control fluid at the reactor outlet. We have also found that, unlike with conventional solid phosphoric acid (SPA) catalyst, where a minimum temperature of 140° C., preferably 155° C., is to be maintained when the catalyst is in contact with the olefin feed, in order to avoid the formation of phosphate esters which leach out, decompose downstream and cause corrosion, such a minimum is not necessary with zeolite catalysts. The lowest reactor temperature, which is typically the inlet temperature, may therefore be as low as 80° C., 100° C. or 120° C., but for reasons of overall heat management may be preferably maintained at or above 140° C. In preferred operations the lowest temperature in the reactor tube is kept at least at 180° C., more preferably at least at 190° C.

The improvements of the present invention are derived from effective control of the reactor temperature profile and also by employing feed delivery conditions, e.g. an inlet pressure, that establishes a minimum reactor outlet pressure of 55 barg. It is believed that these pressure conditions maintain the material in the reactor tubes of the tubular reactor in a single phase which maybe a liquid phase or a dense phase. A significant vapour phase and a two phase system such as a vapour/liquid phase system should preferably be avoided and particularly preferably avoided along the entire length of the tube.

There are several ways to establish whether a known stream composition is subject to a 2-phase flow regime under a particular combination of pressure and temperature conditions. Two experimental ways comprise physically preparing a sample of the particular stream composition and introducing this into a high pressure cell. The desired pressure and temperature conditions are then created inside the cell, typically by compressing the cell volume combined with heating and/or cooling. The content of the cell is made homogeneous for a limited amount of time, by intimate mechanical mixing. The mixing is then stopped and the content of the cell is allowed to come to rest. Several ways may be envisaged to determine whether the fluid in the cell is in a single phase, or is split into a liquid and a vapor phase. If the cell is equipped with an inspection glass, the visual observation of the presence of an interphase is the first indication of whether the mixture composition separates at these conditions into 2-phases or not. Other possible ways may involve audible or electrical signals. Sampling minute quantities of the cell content from the top and from the bottom of the cell, followed by chemical analysis and comparing the analytical results, provides another indication. If materials at the top and bottom of the cell are of the same composition, the fluid in the cell is in a single phase. If the composition of materials at the top and bottom are different, two phases are present in the cell, and the cell content is in a 2-phase regime. The compositional information also provides knowledge about the vapor/liquid equilibrium at the cell conditions. By exploring a sufficiently large area in the Pressure-Temperature diagram, the 2-phase (P,T) envelope for the particular mixture may be determined. The critical pressure and critical temperature may then be read from the diagram where the 2-phase envelope reaches the highest pressure. The equilibrium data may also be used to calibrate the coefficients of a suitably chosen thermodynamic equation-of-state for individual mixture components and also for the mixtures. If sufficient of such thermodynamic data have been determined, the resulting thermodynamic equations may then be used as another way to determine the state of a particular composition under particular pressure and temperature conditions, by simulation using a computer programme. These simulations are commercially available from a number of engineering programming service providers.

We have found that the present invention may be accomplished with extended runs if the feed material is fed to the reactor under a pressure such that the material exiting from the outlet of the tubular reactor is maintained at a pressure of at least 55 barg and thereby the inlet pressure will also be greater than 55 barg. Preferably the outlet pressure is in the range 60 to 80 barg and more preferably at least 65 or 70 or 75 barg.

According to the invention the lowest possible pressure for the tubular reactor outlet is 55 barg. As the composition changes throughout the length of the tube, the two phase envelope in the Pressure-Temperature diagram of the material within the reactor tube changes. The critical point of the reacting mixture moves up in temperature and in pressure as the reaction proceeds. The critical point of the mixture marks a limit to the 2-phase envelope of the mixture, so that at pressures above the critical pressure of a fluid, this fluid is not able to separate into a liquid and a vapor phase, and no 2-phase flow is able to occur, regardless of the fluid temperature. It should be understood that the critical point of the reaction mixture, and its 2-phase envelope, is dependent on the composition. It is therefore dependent on the amount and nature of the olefins and paraffins in the reactor feed, and on the conversion and selectivities obtained during the reaction. We have found that running the process under conditions such that the reactor tube outlet pressure is below 55 barg creates the risk that at some points along the reactor tube, the conditions are inside the 2-phase liquid/vapour envelope. If this happens to a significant degree, it causes the fluid to separate into a vapour and a liquid phase, with the liquid phase containing more of the heavier molecules. Having a vapour phase increases coking rate and therefore catalyst deactivation and hence reduces catalyst life and run length. A 2-phase regime also reduces heat transfer from the inside of the reactor tube to its wall, so that the temperature in the middle of the tube becomes higher, again enhancing the coking rate. In order to reduce the risk of having 2-phase flow regime anywhere in the reactor, the outlet pressure is preferably kept above 60-61 barg, more preferably above 65 barg, and most preferably above 68 barg and is ideally maintained at least at 70 barg for as long as possible in the duration of the reactor run length.

We have also found that the phase behaviour may be further affected by the selection of the diluent that may be added to the reactor feed. We have found that a diluent comprising one or more paraffins having a higher carbon number than the feed olefin is preferred over a diluent with only paraffins of the same or lower carbon number than the olefin feed. During oligomerisation of primarily propylene over a molecular sieve catalyst, the presence of normal butane and/or isobutane in the diluent has been found to improve catalyst life.

We have found that the addition to the oligomerisation feed of an unreactive component, such as an alkane, that has a higher carbon number than at least one of the feed olefins, may also affect the product selectivities over the molecular sieve catalyst. For example, when butanes were used as diluent in the oligomerisation of propylene over ZSM-22 catalyst instead of propane, the selectivity to nonenes increased from about 34% to about 52% wt, while selectivity to the other true oligomers, i.e. hexenes, dodecenes and the minor amount of indirect products all reduced. When the same experiments were performed using ZSM-57 as the catalyst, the nonene selectivity increased from about 64% to about 73% wt, while hexene selectivity also increased from about 3 to about 6% wt, and the selectivities to dodecenes and to the indirect oligomerisation products reduced.

We have found that when an unreactive component, such as an alkane or an olefin oligomer, having a carbon number that is higher than at least one of the feed olefins, is added to the oligomerisation process, it is advantageous to select the carbon number of the unreactive component as being at least one carbon number lower than the carbon number of the lightest of the target oligomer products, preferably at least 2 carbon numbers lower, more preferably at least 3 or even 4 carbon numbers lower. For example, when propylene is oligomerised and the lightest target oligomer is nonene, then the added unreactive component preferably has a carbon number of at most 8, more preferably at most 7, yet more preferably at most 6, even more preferably at most 5, and most preferably it is 4. When butene is oligomerised and octene is the lightest target product, the added unreactive component preferably has a carbon number of at most 7, more preferably at most 6, and most preferably at most 5.

A first advantage is that the unreactive component may then more easily be separated from the lightest target oligomer product by distillation. As a result there will be less of the unreactive component leaving, and thus lost from the process, with the lightest target oligomer, in which product stream it may in addition be considered an impurity that may impair the product quality. A second advantage may be that the added unreactive component may be separated together with the unreacted olefin or olefins, and possibly the alkanes having the same carbon number as the olefin or olefins, and that it may be readily recycled to the oligomerisation reaction with the unreacted olefin, without the need for extra fractionation equipment.

We have also found that the carbon number of the added unreactive component is advantageously chosen as low as possible, as the separation from the lightest target oligomer product by distillation becomes easier. For example, with propylene oligomerisation the added unreactive component is preferably one or more C4 component, such as n-butane or isobutane or a mixture thereof.

We also prefer to keep the space velocity of the olefin feed relatively high, for example above 1 wt/wt/hour, and up to 12 or even 15 wt/wt/hour, preferably from 1-10 wt/wt/hour, more preferably from 2-9 wt/wt/hour and most preferably from 3-8 wt/wt/hour. A high space velocity will improve the heat transfer on the inside wall of the reactor tubes. This, in turn improves the heat transfer from within the reactor tube to the outside of the tube i.e. to the shell side.

Deactivation of a zeolite catalyst during its use to catalyse the oligomerisation of olefins is often believed to be a result of the formation of high boiling polymers as by-products. These by-products can remain on the catalyst and undergo further conversion to higher molecular weight polymers, which resemble heavy tars and in some cases even have the appearance of coke-like material. These materials can coat the catalyst particles and plug pores in the catalyst, thereby causing catalyst deactivation. Accordingly, the process of this invention is ideally carried out at a pressure which is sufficient to maintain a liquid or supercritical (dense) phase of hydrocarbon in contact with the catalyst. This liquid or supercritical hydrocarbon phase maintains conditions whereby the high molecular weight polymers or tar are washed off the catalyst, thereby prolonging the catalyst life. The liquid or dense phase also is more effective in removing heat away from the active sites on the catalyst, thereby suppressing the formation of higher molecular weight polymers or tar.

In the practice of the process of this invention employing a zeolite catalyst, the olefin-containing feedstock is contacted with the catalyst at a temperature, pressure and period of time which are effective to result in conversion of at least a portion of the compounds in the feed to the desired oligomer products. For example, the olefin to be oligomerized may be an olefin from 3 to 9 carbon atoms, preferably from 3 to 6 carbon atoms. The contacting will generally be carried out at a temperature in the range from about 125° to about 300° C. It will be appreciated of course, that the optimum temperature will be a function of the specific reactants employed and their concentration in the feed. The contact temperature will typically be increased over the course of a run in order to maintain economically acceptable overall conversion.

The reactor temperature profile may also be controlled by raising the temperature of the feed to the reactor. The temperature may be raised to, for example, 150° C. to 250° C. such as between 160° C. and 190° C. prior to introduction into the reactor and this may be accomplished by the provision of any suitable heating means. In a preferred embodiment the feed is heated by use of the heat generated in the reactor, such as by the steam, that has been used to control the temperature in the shell side of the reactor, or by the heat contained in the reactor effluent.

When the fresh feed is rich in olefin, the control of conditions within the reactor tube may be effected by running low conversion per pass and recycle of part of the unreacted olefins (mixed with the paraffins of the same carbon number) separated from the reactor tube product stream. The recycle ratio (weight of recycle on weight of fresh feed) may be controlled within a wide range e.g. 0.1 to 2.5, preferably 0.2 to 2.0. For example the ratio can be low, such as 0.2 or 0.3, but can also be higher, such as 0.5, 1.0, 1.5 or 2.0. Typically, the recycle ratio will be selected depending on, for example, the fresh feed composition, the availability (or lack thereof) of another suitable diluent, and any limits on the maximum concentration of olefins in the purge stream. This purge stream contains unreacted olefins and in one arrangement typically comprises all or part of the LPG stream coming from the distillation tower that separates the unreacted olefins and paraffins from the rest of the reaction product after the reactor; such tower is usually called the stabiliser and is often in the first position.

The above-described recycle operation permits the reactor to be operated at a relatively low per-pass conversion, but with a high overall conversion. This enables the overall product yield to be maximised. By way of example, the per-pass conversion may be as low as 50%, and may be achieved by steam drum pressure reduction (in the case where the temperature control fluid is water).

By fresh feed that is rich in olefin is meant for example, in the case of a propylene feed, a feed containing at least 70 wt %, at least 85 wt %, at least 92 wt % or at least 97 wt % propylene. For a fresh butenes feed rich in olefin is meant for example a feed containing at least 65 wt %, at least 80 wt %, at least 90 wt % or at least 94 wt % butenes. Isobutylene may be present in proportions as low as 1 wt % or 0.5 wt % or less; or alternatively in higher amounts such as up to 18 wt % or up to 22 wt % based on total fresh feed.

Hydration can also be introduced as a means of smoothing the reaction, as it tends to temper the reaction rate. It is a less preferred control mechanism, because we have found that water (and other oxygenates) present in the reactor tube can lead to the production of organic acids. These corrode the equipment at various places, in particular in the stabiliser overhead because that is where these compounds tend to concentrate, and it is also where any water in the reaction product tends to concentrate. Sometimes the water can create an undesirable free water phase. The corrosion occurs where the stabiliser overhead vapours start to condense, and also where there is a separate water phase formed. If used, water concentration in the feed may be controlled by conventional means such as a temperature controlled saturator, but preferably by injection.

Feed to the reactor does not need to be absolute dry, but preferably contains 400 wt ppm or less of water, more preferably below 20 wt ppm, most preferably below 10 wt ppm, particularly preferably below 5 wt ppm.

The temperature of the feed at the reactor inlet can be adjusted, as can the space velocity, feed concentration and steam drum temperature (in the case where the temperature control fluid is water) to provide improved control of the temperature profile along the length of the reactor tube. Adjustment of the feed temperature can allow the temperature profile to be smooth over the entire length of the tube. In a preferred operation the feed inlet temperature is raised to a value that is no more than 20 degrees C. below the peak temperature as measured inside the reactor tube. Inlet temperatures can be controlled by independent preheaters, e.g. heated by steam or by reactor effluent.

The temperature along the reactor tube may also be controlled by filling the reactor tube with a more active catalyst in the bottom of the tube (part near the outlet) and a less active catalyst in the upper (inlet) part of the tube. Such an arrangement is disclosed in our co-pending patent application WO2005/118512.

Multiple reactors may be put in series, with the upstream reactors running with colder steam temperatures than the downstream ones. Similar to LPG recycle, this allows running high space velocities over a reactor while still reaching high overall conversions. Therefore, in another embodiment, the process of the invention comprises more than one oligomerisation reactor in series, with the product from one reactor being fed to a second downstream reactor. In such a staged reactor setup, the lead reactor may be operated with a high space-velocity, resulting in the temperature profile being spread out, and the peak temperature being lower, hence resulting in a lower coke deposition rate in that lead reactor. The downstream reactor serves to convert the feed olefins that did not react in the lead reactor. In yet another embodiment, a plurality of oligomerisation reactors is placed in parallel.

Unlike with solid phosphoric acid catalysts, the use of zeolite catalysts provides stable operation and good selectivities at temperatures up to 300° C. Reactor designs allowing such high temperatures also significantly extend the run length before a zeolite catalyst must be removed because of unacceptable activity.

The control of the peak temperature to a value that is no more than 50 degrees C. above the temperature of the temperature control fluid as it exits the reactor, according to the invention, has enabled much improved conversion. Such control may be by controlling the parameters of the temperature control fluid passing through the shell side of the reactor, such as temperature and/or pressure and/or flow rate of the fluid. This controls removal of heat from the reactor tube and so by control of such parameters the temperature difference between peak temperature and temperature control fluid. The Examples in U.S. Pat. No. 5,672,800 give data based on pilot plant (micro-unit) activity, which employs shorter tube length and relatively wider diameter tubes than are preferred in commercial operation. The techniques of the present invention are particularly applicable to operations in which the length to diameter ratio of the tube is at least 50 and in particular at least 100, more particularly from 200 to 300. U.S. Pat. No. 5,672,800 employs lower velocities and has poorer heat transfer to the tube wall.

In most industrial processes such as those described previously, the refinery feed that is to be used in the hydrocarbon conversion reactions will contain impurities such as polar compounds. These impurities would be detrimental to the hydrocarbon conversion reaction and are frequently removed prior to the reaction, by for instance a water wash. In olefin oligomerisation the feeds are frequently subject to a first alkaline wash to remove acidic polar species, such as thiols or mercaptans, followed by a weakly acidic water wash. The last water wash typically produces a feed stream which is saturated with water at the temperature at which the water wash is performed and, accordingly, can be used to provide the water for hydration of the catalyst as is required in the reaction.

Figure 2:
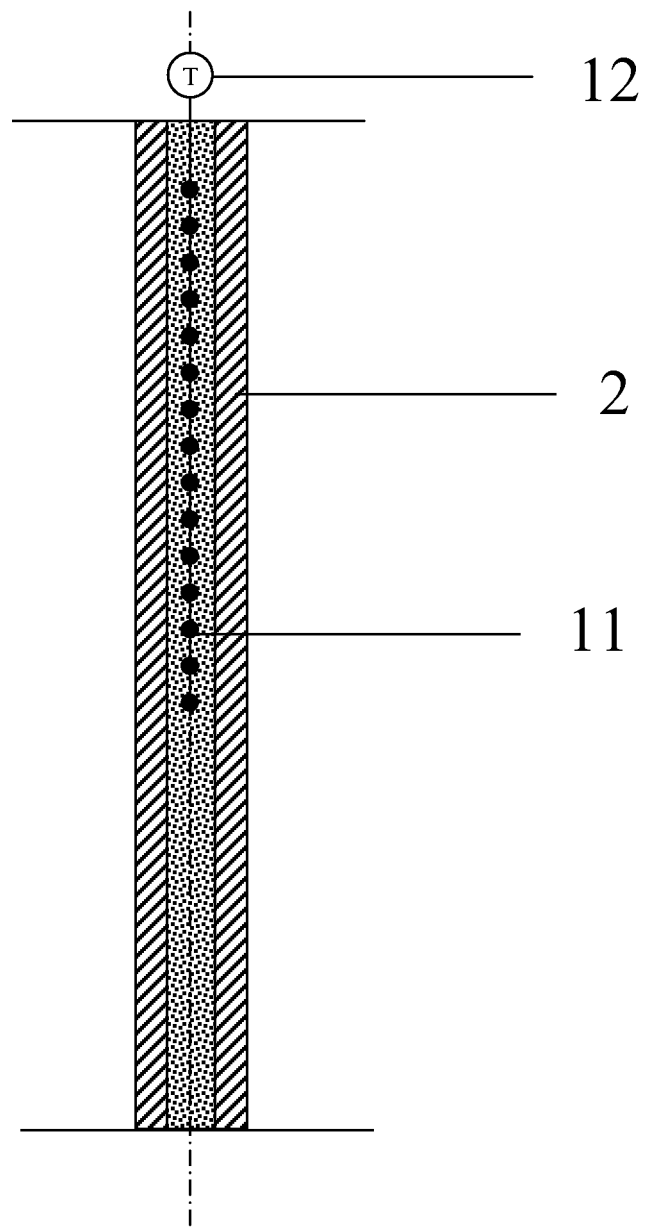
Figure 3:
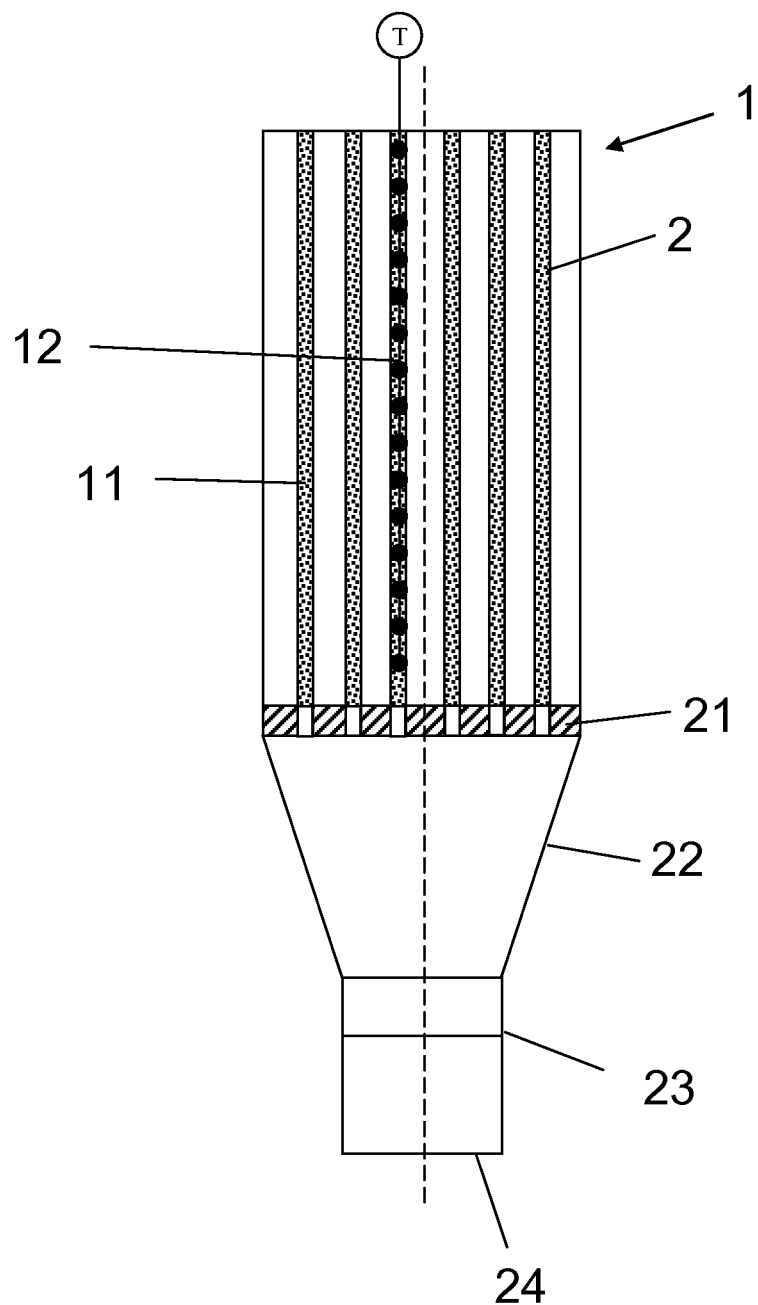
Figure 4:
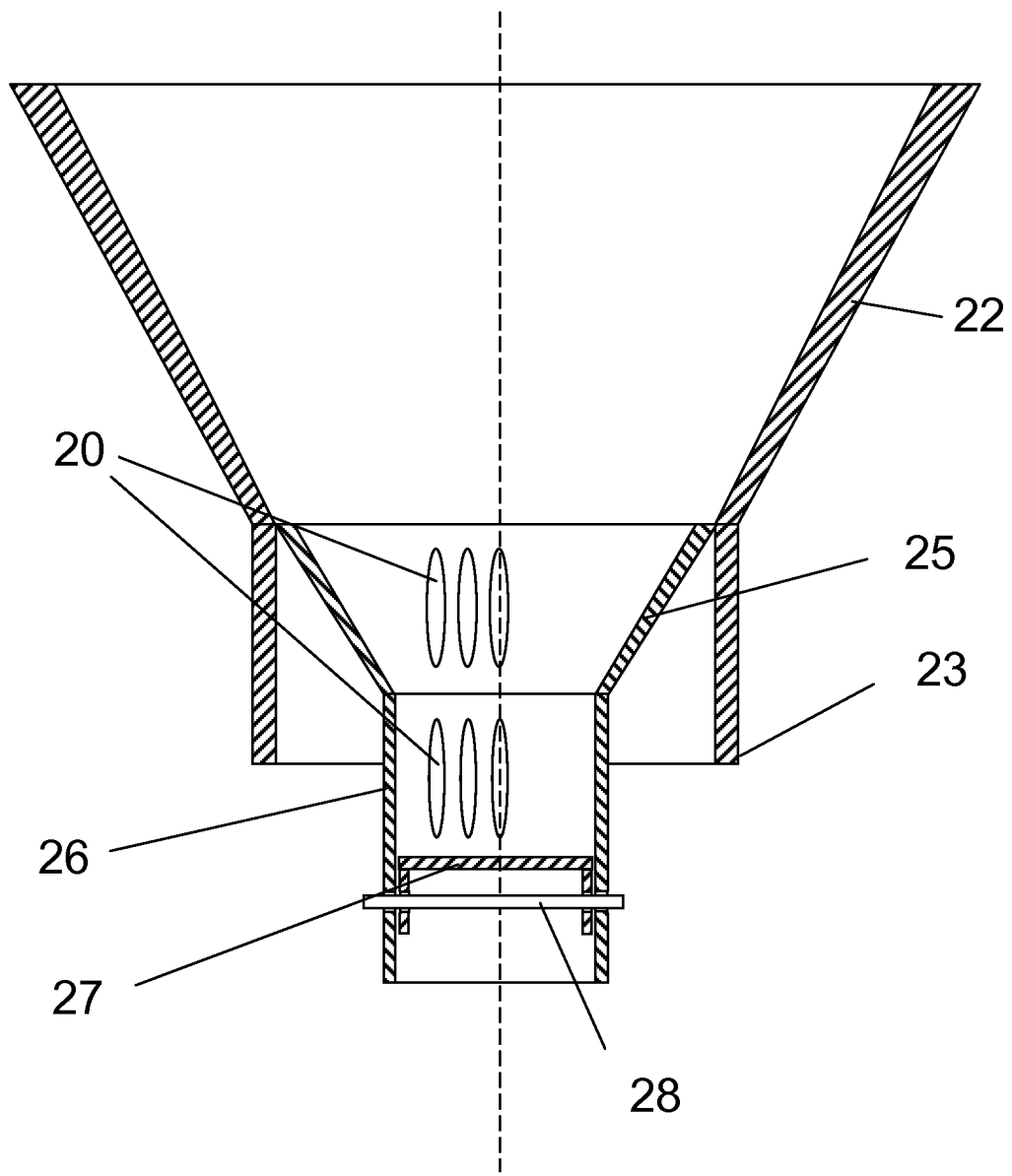
Figure 5:
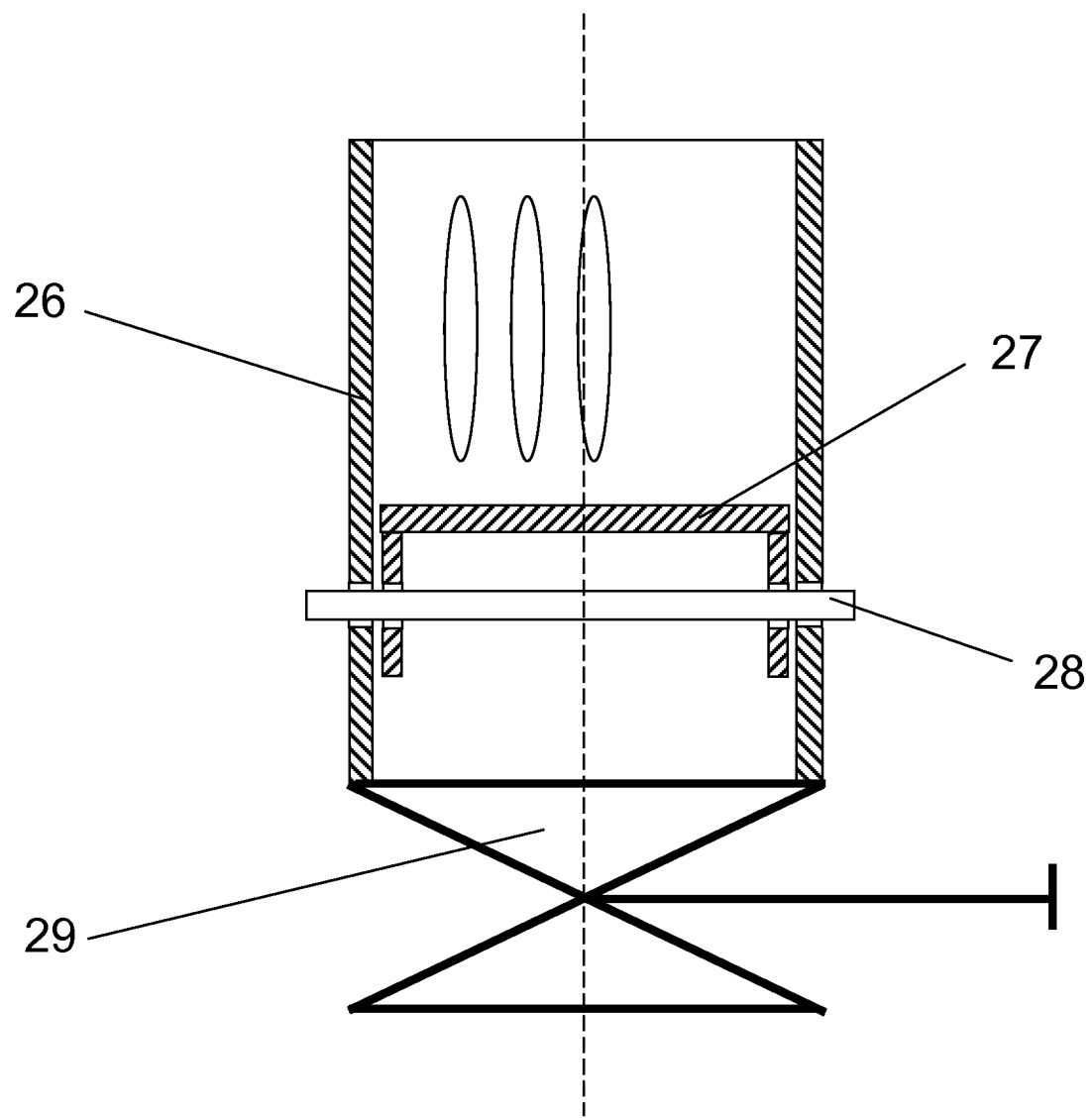

The present invention is illustrated by reference to the drawings in which FIG. 1 is a schematic diagram of the operation of a process according to the present invention, FIG. 2 is a sectional view of a reactor tube that may be used in the process of the present invention. FIG. 3 is a partial view showing the bottom section of the tubular reactor, particularly designed for easy catalyst unloading. FIG. 4 shows the reactor bottom head and details about a straining means internal to the reactor bottom head. FIG. 5 shows details of an extension to the straining means. FIGS. 3, 4 and 5 are discussed together with the catalyst unloading techniques that are preferred by the invention.

FIG. 1 shows a tubular reactor (1) containing a number of reactor tubes (2) inside a reactor shell. Olefin feed is provided at line 3 and may be diluted to the desired level of olefin content. In this embodiment the diluent (4) is shown as being recycled unreacted material from the reaction taking place in the reactor tubes. The feed is preheated in heater (5) and passes to the top of the reactor where it passes into the tubes (2) and downwardly over the zeolite catalyst that is contained within the tubes.

The temperature within the reactor tubes is controlled by generating steam under pressure within the reactor on the shell side. Water passes from the steam drum (6) to the bottom of the reactor through line (7). It is at least partially converted into steam while cooling the tubes in the reactor, as it passes upwardly through the reactor around the outside of the tubes (2).

The steam and water exiting the reactor may be returned to the steam drum (6) through line (8) for phase separation.

The olefin feed passes down the tubes (2), and is oligomerised. The reaction product exits from the bottom of the reactor through line (9) via which it passes to product separation where the olefin oligomer product is removed at (10).

FIG. 2 is a sectional view of a reactor tube (2). The tube (2) is shown filled with molecular sieve catalyst particles (11) and also provided with a 15 point multipoint thermocouple (12) for measurement of the temperature along the initial portion of the tube. The centralising means for keeping the thermocouple substantially at the radial centre of the tube are not shown.

The invention is particularly but not exclusively concerned with processes suitable for the production of $C_5$ to $C_{20}$ olefins boiling in the range of 30° to 310° C., preferably 30° to 300° C., more preferably 30° to 250° C., from propylene and/or butene and/or amylene feedstocks or their mixtures, though ethylene may be present as well. In particular the invention is concerned with the production of the olefins shown in the following table.

TABLE 1

| Oligomer Products | Distillation Range (° C.) ASTM D1078 | |
| --- | --- | --- |
| | Initial Boiling Point | Dry Point |
| Pentenes | 30 | |
| Hexenes | 35 | 72 |
| Heptenes | 88 | 97 |
| Octenes | 114 | 126 |
| Nonenes | 135 | 143 |
| Decenes | 155 | 160 |
| Undecenes | 167 | 178 |
| Propylene Tetramers Or Dodecenes | 175 | 225 |
| Tridecenes | 204 | 213 |

We have found that the hexene products produced over molecular sieve catalysts generally have a higher olefin content than those produced over the conventional solid phosphoric acid catalyst, which provides a higher octane blending value of these hexene products and which makes them preferred as a gasoline component.

The reactor may be provided with means that enable the reactor to be depressurised to flash off water if the water content in the reactor exceeds the desirable level. This can allow the control of water content under circumstances where an undesirable build up of water would, in other circumstances, require the reactor to be decommissioned. Tubular reactor systems are typically equipped with a vacuum system to evacuate the reactor tubes, and this vacuum can be activated to assist the flashing from the catalyst of water and also hydrocarbons. The flashing may also be assisted by stripping with an inert gas, such as nitrogen. More preferably, the flashing from the catalyst of water and hydrocarbons is assisted by pulling a vacuum on the reactor while establishing a flow of inert gas for stripping. We have found it particularly advantageous when the reactor is depressurised and a vacuum is exerted of from 15 to 600 kPa absolute, typically about 60 kPaa, and a flow of nitrogen stripping gas is established that is preferably as high as what the vacuum system allows without the vacuum in the reactor deviating from the typical and desired value. Advantageously the catalyst bed is kept during the flashing at a temperature in the range of 100 to 250° C. We have found that this treatment on a zeolite catalyst enables recovery of some of the activity lost during the run.

Unreacted olefin is generally recycled to the reactor and here again the water content and impurities content of the olefin recycle feed can be monitored and adjusted to optimise the reaction conditions. Alternatively such recycle is mixed with the fresh feed before the water wash step, and hydration control is effected on the combined stream.

The alkenes that may be oligomerised by the processes of the invention include propene, and linear or branched $C_4$-$C_6$-alkenes, which may be mono-, or di-polyunsaturated. The process is particularly advantageous for the oligomerisation of propene and butenes especially isobutylene and may be used for the oligomerisation of a single alkene, or of mixtures of alkenes of the same or of different carbon numbers. The products made by the oligomerisation are mainly the true oligomers of the starting olefins, such as hexenes, but primarily nonenes and dodecenes, when starting from propylene, and octenes when starting from butenes. Other carbon number olefin products are made via side reactions involving cracking of oligomer products to shorter chain olefins that are not the same as the starting olefin(s). As such, propylene oligomerisation may yield an amount of octene product.

We have found that coproduction of octene from a predominantly propylene feed may be desirable, and in such case octene production can be promoted by adding pentenes to the propylene feed to the oligomerisation reaction. However, we have found that this addition of pentenes in propylene oligomerisation may affect the quality of certain products, in particular it may affect the isomer distribution, the specific gravity, the viscosity and the refractive index of the dodecenes or propylene tetramer, and of its derivatives such as isotridecyl alcohol and its adipate and/or phthalate derivative. It is therefore preferred to add not more than about 12% wt of pentenes as a percentage of the total contained olefins in a propylene oligomerisation feed. For consistency of product qualities, it is preferred to have at least 5% wt, more preferably at least 6% wt of pentenes and even more preferably at least 8% wt of pentenes as a percentage of the total contained olefins in a propylene oligomerisation feed.

Oligomerisation of propylene over molecular sieve or zeolite catalyst may give rise to a small amount of pentene product, due to side-reactions or to ethylene in the feed. These pentenes in the reactor effluent may end up in the overhead of a depentenizer tower, optionally together with some more butenes and/or hexenes and even some propylene. We have found that recycling at least part of this depentenizer overhead to the oligomerisation reaction may improve overall olefin utilization and, similar to adding pentenes to the feed, may also have a beneficial effect on the phase behaviour in the reactor and on the catalyst life.

The olefin-containing feeds for oligomerisation may come from a variety of sources, and hence have a wide range of compositions. Traditional sources are steamcracking, catalytic cracking and more recently also methanol-to-olefins processes. The C3 stream from catalytic cracking may, depending on cracking severity, contain for example from 50 to 60% wt of propylene, or higher such as 65% or more, or 70% or above such as 72% wt or 75% wt or even up to 79% wt. The $C_3$ stream from steamcracking may, depending on its sourcing in the steamcracking product cleanup process, contain from 5 to 95 wt % of propylene, for example 92 to 94% wt for chemical-grade propylene, or 25 to 50% propylene for a raffinate byproduct stream from the production of chemical-grade propylene.

Less traditional are propane or butane dehydrogenation processes as sources of oligomerisation feeds. Even less known but suitable sources may be described as follows. Residue gas from the production of isopropanol manufacturing may provide a propylene-containing stream comprising about 5 to 30% wt propylene, typically 6 to 25% wt, more typically 8 to 10% wt propylene, and further comprising from 0.1% wt to 2.2% wt, typically about 0.7% wt of diisopropylether (DIPE) and from 0.04% wt to 0.6% wt, typically about 0.12% wt isopropanol, the remainder mainly being propane but also generally including some C6, C9 and C12 hydrocarbons formed in the isopropanol process. This stream contributes to the diluent effect in the oligomerisation process. In addition, the heavies it contains are removed with the oligomer products, so that they do not appear in the final product propane stream. The oxygenates are precursors for water formation in the reactor, and therefore have to be taken into account for the hydration control.

Cokers and flexicokers may also provide suitable olefin feed streams. In their C3 cut, these typically contain between 35 and 50% wt propylene, typically around 43% wt. In their C4 cut, one typically finds from 14 to 20% wt butene-1, typically about 17% wt, from 7 to 13% wt isobutylene, typically about 10% wt, from 20 to 30% wt of butene-2, typically about 25% wt, from 30 to 40% wt n-butane, typically about 35% wt, and from 5 to 9% wt isobutane, typically about 7% wt. It may also contain about 3 to 5% wt butadiene, a level that may be reduced prior to oligomerisation by selective hydrogenation to n-butenes or n-butane. These coker streams may be used as a mixture of different carbon numbers, in which the C3 cut may represent from 40 to 55% wt of the total mixture, typically about 50% wt, the C4 cut may represent from 40 to 50% wt of the mixture, typically 45-46% wt, and the mixture may further contain up to 3% of C5's, of which about half may be pentenes, and it may also contain a minor amount of ethylene, such as 0.5% wt.

We have found that triple branched octenes in an octene oligomer product may affect the properties and/or the performance of a derivative, such as the viscosity or the UV stability of the di-isononyl phthalate as a PVC plasticiser. Isobutylene in an oligomerisation feed may lead to the formation of triple branched octenes. An increase in the concentration of isobutylene in the oligomerisation feed, such as in a mixed light ends feed stream, may increase triple branching in the octene product. The mixed light ends stream may for example be a mixture of C3 olefins and C4 olefins including isobutylene from for example catalytic cracking, or from steamcracking. The effect of the isobutylene presence on the octene triple branchiness may be reduced by adding pentene to the oligomerisation feed. The less branched octenes made from the pentenes and propylene may then dilute the triple branched octene molecules coming from the isobutylene.

A minimum level of isobutylene in the oligomerisation feed may be desired in some circumstances. Being a more reactive olefin, isobutylene in the feed may lead to a higher selectivity of the higher molecular weight products, such as decenes, undecenes, dodecenes, tridecenes and heavier. These higher molecular weight products may be further hydrogenated and fractionated to provide a variety of isoparaffinic product mixtures, preferred in certain end-uses where high purity and also a low pour point may be desirable. The level of isobutylene in the oligomerisation feed may be used to control the branchiness of these isoparaffinic products, and/or to improve the product performances such as their pour point.

The higher olefins made by zeolite oligomerisation are also used as intermediates for plasticizer range alcohols, for example via cobalt hydroformylation followed by hydrogenation, which may be esterified to provide esters such as phthalates and adipates that are useful as PVC plasticizers. The properties of the ester derivatives are affected by the branchiness of their alkyl chains, and hence by the branchiness of the higher olefin intermediates. The more recently developed molecular sieve oligomerisation catalysts may provide higher olefin oligomers with a different, and depending on the reaction conditions typically a lower branchiness as compared to the more traditional solid phosphoric acid (SPA) oligomerisation catalysts. Having more isobutylene in the feed to zeolite oligomerisation as compared to when solid phosphoric acid is used, may allow the achievement and maintenance of a branchiness of the oligomer products and of their plasticizer ester derivatives that compares closely to what the plasticizer industry has been used to from when SPA catalyst was the oligomerisation catalyst. It may therefore be advantageous to add isobutylene or control its presence in the oligomerisation feed at a higher level when in a particular oligomerisation process the conventional SPA catalyst has been partially or entirely replaced by a molecular sieve oligomerisation catalyst.

Ethylene is less preferred in oligomerisation feeds. It is less reactive because it does not readily form carbenium ions on acidic catalysts. Ethylene may be a precursor in the formation of acetic acid, which may cause corrosion downstream of the oligomerisation reactor, such as in the overheads of the first distillation tower, typically called the stabiliser tower, in which typically the unreacted components are removed from the reactor outlet, and where free water may form. Another effect of ethylene, and of ethane, in the oligomerisation feed, is that a few % of C2 hydrocarbons may have a significant effect on the phase behaviour in the oligomerisation reactor. We have found that it is preferred to have not more than 3% wt, preferably not more than 2% wt of C2 hydrocarbons in an oligomerisation feed that is primarily C3, such as 70% wt propylene, the balance being propane, in order not to create less preferred two-phase behaviour in the oligomerisation reactor, which, as discussed hereinbefore, is a potential cause of more coke formation.

Chlorine compounds, more importantly chlorides, and particularly HCl, are typically also undesired contaminants in oligomerisation feeds, because they may cause corrosion. The combination of a chloride and an organic acid such as acetic or propionic or butyric acid may cause higher corrosion rates than each of these components by itself.

The zeolite catalyst used in the present invention may be any zeolite that is active in alkene oligomerisation reactions. To the extent that a particular molecular sieve catalyst is active for alkene oligomerisation, the current invention also applies to the molecular sieve catalyst. For example, there may be used a catalyst selected from the group consisting of zeolites of the TON structure type (for example, H-ZSM-22, H-ISI-1, H-Theta-1, H-Nu-10, KZ-2) or zeolites of the MTT structure type (for example H-ZSM-23, KZ-1) or zeolites of the MFI structure type (for example, H-ZSM-5) or zeolites of the MEL structure type (for example, H-ZSN-11) or zeolites of the MTW structure type (for example, H-ZSM-12), or zeolites with the EUO structure type (for example, EU-1), or zeolites H-ZSM-57, or any member of the ferrierite structure family. Other examples of suitable catalysts are offretites, H-ZSM-4, H-ZSM-18 or zeolite Beta. Reference is made to 'Synthesis of High-Silica Aluminosilicate Zeolites' by P. A. Jacobs and J. A. Martens (published as volume 33 in the series 'Studies in Surface Science and Catalysis') for a review of the synthesis and properties of the aforementioned zeolites.

Additionally, the catalyst can be a zeolites synthesised without addition of a template, for example, faujasites, zeolite L, mordenites, erionites and chabazites, the structures of which are contained in the 'Atlas of Zeolite Structure Types' by C. Baerlocher, W. M. Meler and D. H. Olson (published by Elsevier on behalf of the Structure Commission of the International Zeolite Association, $5^{th}$ Revision Edition, 2001). Zeolite catalysts having crystal structures that are essentially the same as the crystal structures of the above-mentioned zeolite catalysts, but differing slightly therefrom in chemical composition, may also be used. Examples include zeolite catalysts obtained by removal of a number of aluminium ions from, or by steaming of, the above-mentioned zeolites catalysts: and zeolite catalysts obtained by the addition of different elements (for example boron, iron and gallium), for example, by impregnation or cation exchange, or by incorporation during the zeolite synthesis.

Mixtures of two or more zeolites e.g. a mixture of ZSM-22 and ZSM-57 or ZSM-22 and ZSM-5 can be used as disclosed in EP 0746538 B1. Or alternatively, upon the surface of each zeolite crystal, a layer of another zeolite can be deposited as disclosed in EP 0808298 B1.

The zeolite conveniently has a crystallite size up to 5 µm, such as within the range of from 0.05 to 5 µm, for example from 0.05 to 2.0 µm, and typically from 0.1 to 1 µm. An as-synthesized zeolite is advantageously converted to its acid form, for example by acid treatment, e.g. by HCl, or by ammonium ion exchange, and subsequently calcined before use in the process of invention. The calcined materials may be post-treated, such as by steaming. It is also possible to use, as is known in the art, a material in which silicon and aluminium have been replaced in whole or in part by other elements. Silicon may, for example, be replaced by germanium and/or phosphorus; and aluminium more especially by boron, gallium, chromium or iron. Materials containing such replacement lattice elements are also generally termed zeolites, and the term is used in this broader sense in this specification. The zeolites might be supported or unsupported, for example in the powder form, or used as an extrudate with an appropriate binder. Where a binder is employed, the binder is conveniently a metal oxide, such as alumina or silica and is present in an amount such that the oligomerisation catalyst contains for example from 1 to 99 wt % of the zeolite, more preferably from 50 to 70 wt %.

We prefer to apply vacuum to the reactor shortly after it is taken out of service. We have found that this removes residual hydrocarbons, preventing the build up of even heavier hydrocarbons and permitting easier removal of the catalyst. The removal of residual hydrocarbons may also be assisted by stripping with an inert gas, such as nitrogen. We have found it particularly advantageous when the reactor is depressurised and a vacuum is exerted of from 15 to 600 kPa absolute, typically about 60 kPaa, and a flow of nitrogen stripping gas is established that is as high as the vacuum system allows without the pressure to deviate from the typical or desired value. Advantageously the catalyst bed is kept at a temperature in the range of 100 to 250° C. also during this removal step.

This may be because hydrocarbons rapidly vaporising on the catalyst surface break up the agglomerates formed during operation. It has also been found beneficial to include such a flash-off or vacuum treatment in the procedures following an emergency or standby shutdown of the reactor, as it removes a significant portion of still reactive hydrocarbons from the catalyst. It therefore reduces coke build up by preventing condensation reactions on the catalyst. We have found that with this procedure, the catalyst in the reactor typically will retain or gain activity, compared to pre-shutdown, when it is subsequently put into service again after the emergency or standby shutdown.

Selected streams can also be recycled to the reactor to effect dilution or to modify the product slate. For instance, in a propylene fed reactor, $C_6$, $C_9$ or $C_{12}$ olefin streams, fractionated downstream of the reactors, can be recycled to the reactor to modify the product slate distribution. For example, recycling hexenes may increase nonene selectivity, and recycling nonenes may increase propylene tetramer selectivity. Byproduct streams of carbon numbers other than the above, such as $C_{7-8}$ or $C_{10-11}$ mixtures, can also be recycled to reduce their production, if possible even recycled to their full extinction. The feed to the reactors may also be diluted with such recycle streams. These recycle streams may be introduced in order to achieve one or more effects, e.g. to affect phase behaviour in the reactor, to improve catalyst life, to control conversion, to control the selectivity towards particular products, and to assist in control of the exotherm and therefore also the peak temperature.

A problem that may occur with tubular reactors is that the circulation flow of the shell side temperature control fluid is not sufficiently high. In the case of water and steam, this means that there is a high rate of vaporisation within the reactor on the shell side, such that much of the volume in the upper side of the reactor shell side and in the return line to the steam drum is occupied by steam vapor instead of by boiling water. This may impair the heat transfer in the upper part of the reactor tube or bundle of tubes, which makes the temperature profile inside the tube sharper and more difficult to control within the range required according to the invention. When colder boiler feed water is introduced in the steam drum below the liquid level, the temperature of the water flowing from the steam drum to the reactor shell side may become subcooled to below its boiling temperature, which also impairs heat transfer at the lower end of the tube bundle because the heat exchange is not immediately in the boiling regime. We have found that this problem may be alleviated by the solution suggested in our copending patent application number PCT/US06/06014 filed 21 Feb. 2006.

An alternative way to control the temperature profile along the reactor tube, is to have the shell side temperature control fluid flow in co-current mode with the process fluid which can provide the temperature control fluid at its lowest temperature close to the position where the process fluid is at its highest temperature. This may be achieved by forcing the circulation of the water from the steam drum from top to bottom on the shell side in the case where the reactor tubes are arrayed vertically with their inlets at the top. This creates a risk of vapor pockets on the shell side, but this may be alleviated by providing vent tubes returning to the steam drum. It may alternatively be accomplished by having the process fluid moving upwards inside the reactor tubes while the temperature control fluid flows from bottom to top, for example by forced flow or simply driven by thermosyphon.

Molecular sieve oligomerisation catalysts typically provide a wider operating window, with temperatures up to 300° C., as compared to the conventional SPA catalyst, which are typically constrained to an average temperature of about 245° C. When the molecular sieve catalyst is retrofitted in process equipment that was designed for SPA catalyst, the part of the temperature window between 245 and 300° C. is typically not available, due to equipment constraints. This temperature window may be of particular interest because of improved qualities of the oligomers produce therein, such as a lower branchiness. In particular with tubular reactors that raise steam on the shell side, the constraint may be imposed by a maximum design pressure on the shell side or of the steam drum. The design temperature limitation is typically less severe, and is more readily overcome when the equipment was provided with extra metal in the wall thicknesses, typically included for extra safety reasons and in older designs because of empirical design methods. The design methods may since have been refined, and current wall thickness tolerances may be significantly lower than in the older designs. This design pressure constraint may in such cases be circumvented by replacing the water as the temperature control fluid by a different compound or mixture, in particular a fluid that has a lower vapor pressure than water at the desired temperatures between 245 and 300° C. It may provide a broader operating temperature window for the molecular sieve catalyst, which may extend the run length before the catalyst needs to be regenerated or replaced.

The major advantage of molecular sieve catalysts as compared to SPA catalyst, is the fact that they can be regenerated. During regeneration the heavy tar-like materials and high boiling polymer byproducts may be removed and catalyst activity may be at least partially restored. The removal is typically performed by controlled burning or oxidation, bringing the deactivated catalyst in contact with an oxygen containing gas, typically air which may be diluted with nitrogen to control the oxidation or burning rate.

We have also found that at the end of a run, a molecular sieve catalyst or zeolite is typically still free-flowing. The conventional SPA catalyst is typically swollen and coked up at the end-of-run, and needs to be drilled out, typically from the top of the reactor, or in some circumstances even blasted out by using high pressure water jets, i.e. by hydroblasting. The SPA catalyst typically rests on a layer of small stones in the bottom of the tube, at least as high as the thickness of the bottom tubesheet and e.g. about 15 cm high, which stones rest on a wire mesh that rests on a metal plate holding in place the wire mesh and perforated with holes typically corresponding in location, and optionally also in internal diameter, with the end of the reaction tubes sticking through the tubesheet of the reactor shell. When the reactor containing the SPA catalyst needs to be unloaded, the heavy bottom head needs to be unbolted and removed, as well as the metal plate and the wire mesh, and preferably the layer of stones is then removed by mechanical means or agitation and collected. The softer SPA catalyst is then drilled out from the top of the reactor, from which the head is also removed. By applying vacuum on the tube that is being drilled, from the top of the reactor, the SPA catalyst particles are carried upwards with the flow of air coming in from the bottom of the tube, and may be separated from the air flow and collected for disposal. The SPA catalyst particles are typically not suitable for regeneration or recovery, and are generally disposed as landfill. This catalyst removal process is very time consuming, and typically takes about 8 hrs per metric ton of catalyst.

We have found that with the free flowing molecular sieve or zeolite catalysts, it is not necessary to use a drill or hydroblasting, but it is now possible to simply vacuum out the free flowing catalyst pellets, with a technique conventionally identified as "vacuum lean phase pneumatically conveying", from the top of the reactor. The unloading process goes much faster than with SPA catalyst, and typically takes not more than about 4 hrs per ton of catalyst. The catalyst pellets are collected from the pneumatic conveying system and may be regenerated. However, due to the attrition during the molecular sieve particle conveying, typically about 4% of the catalyst ends up as catalyst fines, which may have to be discarded and replaced by fresh catalyst. Because of the high manufacturing cost of these catalysts, this represents an economic burden.

We have found that with the free flowing molecular sieve or zeolite catalysts, it is advantageous to change the design of the reactor so that the catalyst removal may be done in a much shorter time, while at the same time loss of catalyst by attrition into catalyst fines may be minimized. This design is illustrated by FIGS. 3, 4 and 5. Referring to FIG. 3, we prefer to provide the reactor (1) with a bottom head (22) that has a bottom opening provided at or near its lowest point. This opening may then be provided with a bottom flange (23) onto which may be bolted a cover (24) or preferably the reactor outlet line (9, not shown in FIG. 3). We prefer the bottom opening to have a diameter sufficiently large for letting the catalyst particles and any inert material particles pass, such as having a diameter of at least 5 times, but preferably at least 10 times, more preferably at least 15 or 20 times and even more preferably at least 25 times the largest particle diameter of the solids in the reactor. Referring to FIG. 4, the bottom head (22) is preferably provided with a straining means (25) to withhold the solid particles in the reactor from passing further down and/or downstream in the process. We prefer to have the straining means to be provided at the bottom opening. We also prefer to fill the internal volume above the straining means and below the reactor bundle with inert material particles such as ceramic balls.

More particularly, and as illustrated in FIG. 3, we prefer to have the bottom part of the reactor tubes, at least the lengths of the tubes (2) that are in contact with the bottom tubesheet (21), typically about 15 cm, also filled with inert material particles. The molecular sieve catalyst particles (11) are then loaded on top of the inert material particles, in the reactor tubes (2). We prefer the inert material to have a different, preferably a larger size than the catalyst particles. The inert material particles preferably have dimensions such that the average smaller particle diameter is at least 1.5 times, more preferably at least 2 times, even more preferably at least 2.5 times and most preferably at least 3 times and not more than 5 times the average smaller diameter of the typical zeolite catalyst pellet. Returning to FIG. 4, we prefer the straining means (25) to have a funnel shape, and we also prefer the walls of the straining means to have perforations (20), to let the reactor fluid content pass but with holes sufficiently small to withhold the solid particles. These perforations (20) may be circular holes, but are preferably elongated slots, in particular when the inert material particles are ball-shaped, like with ceramic balls. Such elongated slots are very effective for letting a fluid pass while retaining ball-shaped particles.

A part of the straining means (25), preferably a part around the centre, extends, preferably as a cylindrical sleeve (26), downwards to below the reactor bottom flange (23), such that good manual access may be provided from below the reactor to the lower part of the outer side of the downward extension (26), when the bottom cover is opened or the outlet connection is removed. That extension (26) preferably has perforations (20), and is preferably foreseen internally with a fitting withholding device (27), such as a plate or a drop cap inside the funnel tube, sufficiently fitting for blocking the solids but sufficiently loose for allowing it to be moved up and down the sleeve. The withholding device (27) is preferably held up by at least one support means (28) that may be removable from the side of the extension (26) underneath the straining means (25). This withholding device (27) could be for example a drop cap inside the cylindrical funnel tube that is supported by a single rod passing through the drop cap and passing and extending through two holes at opposite locations in the funnel tube wall, such that the rod is accessible from the outside of the funnel tube and removable by pulling or pushing it through the holes in the funnel tube wall. We prefer that part of the withholding device (27), such as the blocking plate or the top of the drop cap, to also have perforations (not shown) similar to the rest of the straining means, such as the funnel wall, such as also having elongated slots through which the ceramic balls cannot pass but fluid readily can. We prefer the cross section of the extension (26) to have a diameter sufficiently large for letting the catalyst particles and any inert material particles readily pass, such as having a diameter of at least 3 times, but preferably at least 5 times, more preferably at least 7 or 8 times and even more preferably at least 10 times the largest particle diameter of the solids in the reactor.

Preferably, as illustrated in FIG. 5, the extension (26) of the straining means, such as the end of the funnel tube, is provided with means to fasten a device for variably restricting solids flow (29, the device being only shown schematically). When the reactor needs to be unloaded, the reactor fluid content is drained and the reactor is prepared for opening, the cover (24) or the section of the outlet line (9) connected to the reactor bottom opening may be unbolted from the bottom flange (23), and a device for restricting solids flow (29) may be fastened to the extension (26) of the straining means (25). The device for restricting solids flow may preferably be such that it is capable of also stopping solids flow, and it is advantageous that it may also restrict solids flow partially. We prefer to use a gate valve or slide valve which allows a quick change from no solids flow to maximum solids flow, but also allows partial restriction of the solids flow to control the solids flow rate. To the restricting device (29), we prefer to attach a shute or hose for guiding the solids passing through the extension (26) of the straining means (25) into a container.

When the restricting device (29) is fastened to the extension (26) of the straining means (25), and optionally the solids shute is attached, at least one of the removable support means (28) for the withholding device (27) is removed, so that the withholding device (27) drops on top of the restricting device (29). The solids on top of the withholding device (27) follow and also drop. The restricting device (29) is then opened fully for a short period and again closed, and the withholding device (27), accompanied by a small amount of the solid content of the reactor, typically a small part of the inert material particles, falls through the restricting device (29) and the withholding device (27) may be recovered for future reuse.

The reactor free-flowing solids content may then be drained by opening the restricting device (29), optionally controlling or intermittently stopping the solids flow, and the particles may be collected in a container placed underneath, or, provided the catalyst particles have a different dimension than the inert material particles, the two may be separated and separately collected by means of a sieve having the suitably sized openings. We have found that this design of the reactor bottom and unloading facilities allows to empty a reactor in a period of less than 1 hour per ton of catalyst, typically at a rate of at least 10 metric tons per hour. We have also found that this unloading method causes less attrition damage, and attrition losses to catalyst fines may be kept at 1-2% or below, and this over the entire cycle of reactor unloading, regeneration and reloading, including any transport and handling operations. The lower mechanical damage caused by this unloading method provides the additional advantage that less tough catalyst particles may be used, which may be smaller in size, such as e.g. 1.6 mm diameter extrudates, but which are less susceptible to mass transport limitations during their use, and hence provide a higher catalyst activity.

We have found that it is advantageous that any of the surfaces in contact with the solid particles in the reactor, particularly those surfaces supporting the particles in the reactor bottom head (22), as well as those in the straining means (25) with the exception of the withholding device (27), preferably have an inclination that is at least equal to the highest angle of repose of any of the solid particles in the reactor, such as the catalyst particles or the inert material particles, whichever has the highest angle of repose. This brings the advantage that pockets of solids do not remain in the reactor after the unloading of the catalyst. We prefer that the surfaces have an inclination that is at least 10°, more preferably at least 15° higher than this highest angle of repose. We prefer that the reactor bottom head (22) is cone shaped, and optionally comprises cone-shaped sections; and that the straining means (25) has a funnel shape.

We have also found that regeneration may not restore the activity of the catalyst to the same level as a fresh catalyst. We therefore prefer to load the regenerated catalyst in the top of the tubes of the reactor, on top of any fresh catalyst that is preferably loaded in the bottom of the tubes. This brings the advantage that the temperature in the top of the tube is rising less steeply due to the lower catalyst activity, and this contributes to a lower peak temperature in the tube.

We have also found that regenerated catalyst may not anymore have the same selectivity as a fresh catalyst. But we have found that the way of loading just described almost completely corrects for that deviation, such that the combination of regenerated catalyst on top of fresh catalyst provides the selectivity of an entirely fresh catalyst load, and minimises or substantially avoids any selectivity disadvantage that would be brought by the regenerated catalyst.

The industrial molecular sieve oligomerisation catalysts are typically in the form of extrudates. The handling of the catalyst during unloading, regeneration and reloading causes attrition and the formation of smaller catalyst particles. If these smaller regenerated catalyst particles are loaded on top of regular size fresh catalyst particles, the two may be readily separated by sieving, at or after unloading, which provides the capability to give the two separated parts a different regeneration treatment if so desired, or alternatively discard one part and regenerate the other part.

We have also found that molecular sieve oligomerisation catalysts such as ZSM-57 may have a higher activity than the conventional SPA catalyst. This may lead to a steeper temperature rise in the top of the tube, a higher peak temperature, and a faster deactivation and shorter catalyst life. This problem may be alleviated, in the case where mixed molecular sieve and SPA catalyst is used, by loading the highly active molecular sieve catalyst only in the bottom of the tube, and load SPA catalyst on top of the molecular sieve. The lower activity of the SPA catalyst will slow down the temperature rise in the top of the tube, and reduce the peak temperature. The high activity of the molecular sieve catalyst is therefore mitigated as the reacting fluid will have become less reactive by the time it reaches the molecular sieve. The SPA catalyst also may act as a guard bed for impurities affecting the molecular sieve by adsorbing them or reacting them into components that do not affect the molecular sieve. The two catalysts may preferably be separated by an intermediate layer. This may allow for a partial drilling of the top SPA catalyst layer, replacing it with fresh SPA catalyst and restarting the reaction. Only when the performance of the longer lasting molecular sieve catalyst has also deteriorated, may all catalyst be discharged and the molecular sieve regenerated. A disadvantage of this arrangement may be that the SPA catalyst hydration requirement may impose a required level of water in the reactor feed that is less optimal for the molecular sieve catalyst, and the activity of the latter may suffer somewhat because of that. Another possible disadvantage of this catalyst arrangement may be a leaching of phosphoric acid from the SPA catalyst and attacking the molecular sieve by removing the aluminium atoms from the framework and reducing the number of active sites. In order to avoid that the leached phosphorus reaches the molecular sieve catalyst, an intermediate trap of for example a base such as ZnO or calcium carbonate may be foreseen to catch the phosphorus and/or phosphoric acid that may possibly leach.

In the practice of the invention, when starting up the process the fixed bed of zeolite catalyst within the reactor tube may be initially immersed in a start-up fluid. This typically comprises a less reactive or inert hydrocarbon liquid, such liquid preferably being circulated through the reactor to provide heat to the catalyst bed. The desired conditions of temperature and pressure, are then established in the fixed bed of zeolite catalyst. A minimum temperature may also be required before start-up, to minimize or eliminate certain side reactions that could occur with reactive feed on insufficiently heated catalyst. A flow of the feedstock, which may be hydrated, is then introduced over the catalyst bed under the conversion conditions that were previously established when the catalyst was immersed in the start-up fluid.

However, the use of a circulating start-up fluid is not essential as the heat up of the catalyst bed can be accomplished via the temperature control fluid on the shell side of the reactor. When the desired temperature is reached, normal feed may be introduced into the reactor.

The start-up feed comprises an olefin, optionally a diluent, and optionally an appropriate amount of water. The relative proportions of the materials in this feed depend upon the nature of the olefin and the oligomerisation conditions. The reactions are strongly exothermic and accordingly a diluent such as a paraffinic or a heavy olefinic hydrocarbon is generally used. For example when the feed consists of $C_3$ olefins, we prefer that the feed contain from 40 or 42% to 60% or 65%, or 80% or 90% or 95% e.g. 48 to 52% by weight of olefins, with the balance being a paraffinic or a heavy olefinic hydrocarbon diluent, such as a $C_3$-$C_5$ refinery paraffinic stream. Such feeds may be readily available as that which may be obtained from a catalytic cracker. Its olefin content may be reduced if needed by recycling of unreacted paraffins or low olefinic streams found elsewhere or recovered from the reactor effluent. If butene is to be oligomerised we prefer to use a feed containing up to 80%, more preferably up to 70% or up to 60% olefins, e.g. from 50% to 70% olefins.

The materials obtained from the process of the present invention will generally be a mixture of desired olefin oligomers, unreacted olefins, diluent (if any is used), water and other impurities. The materials are therefore separated, generally by fractional distillation primarily into the olefin oligomers, the unreacted olefins and, if present, the diluent. The unreacted olefins and diluents may be recycled to the oligomerisation reactor. The olefin oligomers may then be purified as required for use in subsequent reactions. For example the oligomers may contain trace amounts of sulphur which may damage a hydroformylation catalyst. Accordingly, if the olefins are to be used as a feed for hydroformylation, the feed may need to be desulphurised. Similarly the olefin oligomers may contain trace amounts of chlorine which may also be detrimental to hydroformylation catalysts and may need to be removed. If the hydroformylation catalyst is not damaged by sulphur or chlorine, the catalyst in the subsequent hydrogenation step to produce the alcohol derivatives may be damaged by these compounds, and hence sulphur and chlorine are preferably removed, most preferably to very low levels. Furthermore the olefin oligomers themselves are frequently mixtures of oligomers of different carbon number. For example oligomerisation of a mixture of propylene, butene and amylene can result in a mixture of $C_6$ to $C_{13}$ oligomers and this mixture can then be separated by fractional distillation to obtain the oligomer or oligomer mixtures desired for a particular purpose.

In a highly preferred embodiment, the process of this invention can be used in connection with the conversion of a mixture of $C_3$ and $C_4$ olefins to gasoline blending stock by oligomerisation. In such an embodiment, the feed will be comprised of at least about 25% by weight of olefins. A typical olefin-containing feedstock to a polymerisation unit for conversion to oligomers in the gasoline boiling range will comprise a mixture of propane, butane, 2-methylpropane, propene, 1-butene, 2-butene and 2-methylpropene, wherein the olefin concentration is in the range from about 35 to about 60% wt. Ethylene and ethane may also be present, albeit typically in minor amounts. However it will be appreciated that the olefin-containing feedstock can have a variety of other compositions which include but are not limited to, other olefins or olefin mixtures, other diluents and the presence of a minor amount of aromatic compounds. In addition olefin concentrations can be used which are outside this range.

In a further embodiment the present invention is used for the oligomerisation of olefins such as ethylene, propylene, butenes and amylenes to produce $C_6$ to $C_{13}$ olefins which can be used as feeds for hydroformylation reactions for the production of aldehydes and alcohols. The aldehydes may then be oxidised to produce acids or hydrogenated to produce alcohols. The alcohols may then be used in the production of synthetic esters such as plasticiser esters or synthetic lubricants or in the production of surfactants. The olefins may be hydroformylated using low pressure rhodium catalysed hydroformylation technology or high pressure hydroformylation technology which is typically cobalt catalysed, but rhodium is also used. The present invention is particularly useful in the production of feedstocks which are hydroformylated in the manner described in WO 2005/058787. Where the aldehydes produced by this method are hydrogenated, this may readily be accomplished by the method described in WO 2005/058782. The aldehydes may be oxidized to the corresponding carboxylic acids. Both the acids and the alcohols may be esterified to esters. These esters may be plasticizer esters for PVC, such as phthalates, adipates or trimellitates, or they may be lubricant esters or lubricant additive esters such as polyol esters. A suitable esterification process is described in WO 2005/021482 or our copending application PCT/EP2006/005068, filed 24 May 2006. The oligomers may also be hydrogenated to alkanes, which may be used as low sulphur, low aromatic, low pour point hydrocarbon fluids suitable in end uses such as solvents and thinners in paints, printing inks, as stove fuels, or as process fluids or carriers in polymerization processes.

In the present invention the catalyst is contained in a reactor tube, generally a multiplicity of tubes which are surrounded by a circulating cooling medium. Preferably these tubes will each typically have an internal diameter of from about 25 mm to about 75 mm as previously discussed, although other diameters can also be used. A tubular reactor is frequently preferable to a chamber reactor because it permits a closer control of the reaction temperature and can be easily constructed for high pressure operation. Ordinarily a plurality of reactors will be used. For example an olefin oligomerisation unit employing tubular reactors can have as many as eight or more reactors. The temperature in tubular reactors is typically controlled by steam generation in the shell around the reactor tubes. Multiple tube bundles may have their shell side linked up to the same single steam drum.

The invention claimed is:

1. A process for oligomerising an olefin comprising contacting the olefin with a zeolite catalyst in a reactor tube of a tubular reactor having a shell that contains a temperature control fluid for removing heat of reaction from the reactor tube, in which process the olefin feed to the reactor contains at least 42 wt % of olefin, wherein operating conditions are controlled such that the reaction product mixture exiting the reactor is at a pressure of at least 55 barg and wherein the shell side temperature control fluid parameters are controlled such that the peak temperature in the reactor tube is no more than 20 degrees C. above the temperature of the temperature control fluid as said fluid exits the reactor, wherein said process further comprises using a diluent and said diluent comprises an unreactive component having a higher carbon number than at least one of the feed olefins.

2. The process according to claim 1 in which the olefin feed contains up to 65 wt % propylene.

3. The process according to claim 1 in which the feed contains up to 80 wt % butene.

4. The process according to claim 1 further comprising measuring the peak temperature by means of a multipoint thermocouple disposed in the reaction tube.

5. The process according to claim 1 further comprising maintaining the peak temperature below 260° C.

6. The process according to claim 1 in which the reactor product exits the reactor tube at a pressure in the range 60 to 80 bang.

7. The process according to claim 1 further comprising operating at an olefin teed space velocity of from 1-15 w/w/h.

8. The process according to claim 1 in which the temperature of the feed entering the reactor tube is between 150° C. and 250° C.

9. The process according to claim 1 further comprising accomplishing control of the temperature control fluid parameters by adjusting at least one of the parameters selected from the group consisting of the temperature, the pressure and the flow of said fluid to remove heat from the reactor tube and maintain the peak temperature in the desired range.

10. The process according to claim 1 in which 1 feed to the reactor contains 400 ppm wt or less of water.

11. The process according to claim 10 in which the feed contains below 20 ppm wt of water.

12. The process according to claim 1 in which the reactor tabes are of internal diameter from 25 to 75 mm.

13. The process according to claim 1 in which the reactor tube has a length to internal diameter ratio of at least 50.

14. The process according to claim 1 in which the tubular reactor comprises a plurality of reactor tubes arranged vertically and further comprising introducing the olefin feed at the top of the tubes and passing through the tubes in a downward direction.

15. The process according to claim 1 in which the temperature control fluid flows within the reactor shell counter current to the direction of the flow of the olefin feed within the reactor tube.

16. The process according to claim 1 further comprising maintaining the fluid material contained within the reactor tube substantially in a phase selected from the group consisting of a single liquid phase and a single dense phase and mixtures thereof.

17. The process according to claim 1 wherein the reactor tube comprises a thermocouple.

* * * * *